March 2, 1943. B. D. DRAIN Plant Pat. 570
STRAWBERRY PLANT
Filed Oct. 10, 1941
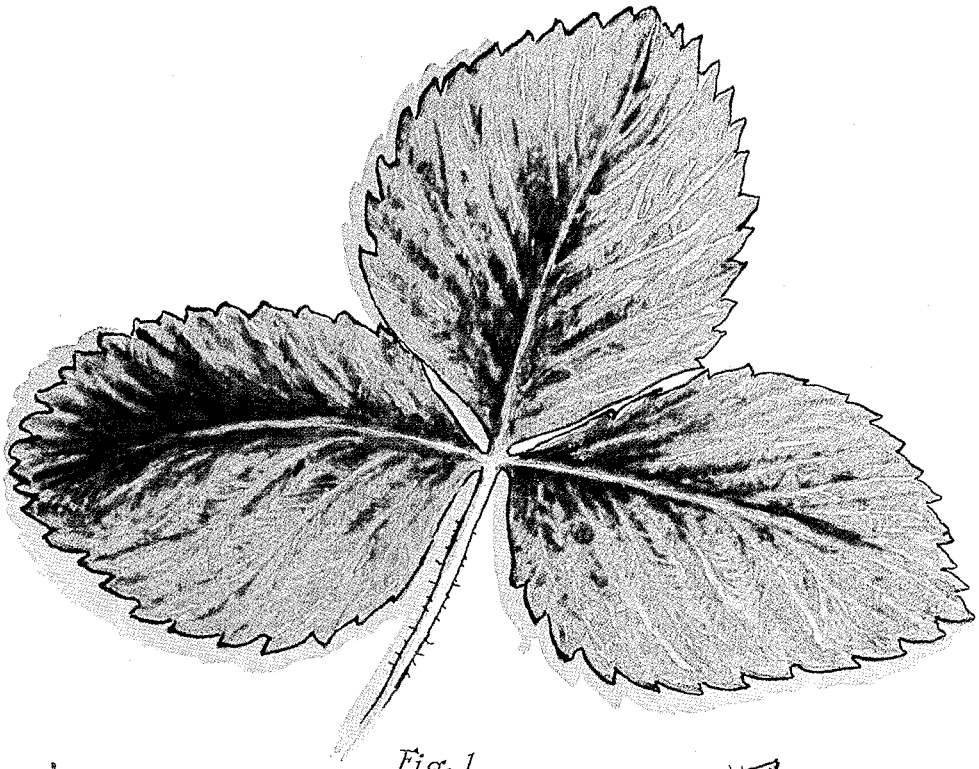
Fig. 1
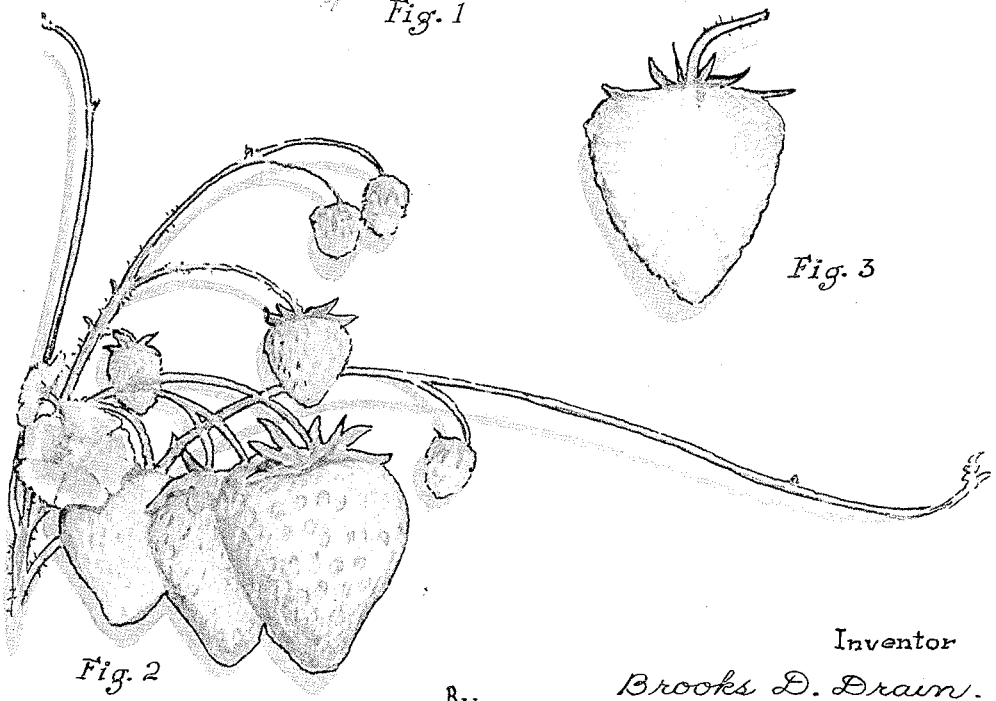
Fig. 2
Fig. 3
Inventor
Brooks D. Drain.
By Cameron, Kerkam & Sutton.
Attorneys.

Patented Mar. 2, 1943

Plant Pat. 570

UNITED STATES PATENT OFFICE

570

STRAWBERRY PLANT

Brooks D. Drain, Knoxville, Tenn., assignor to The University of Tennessee Research Corporation, Knoxville, Tenn., a corporation of Tennessee Application October 10, 1941, Serial No. 414,531

1 Claim. (Cl. 47—62)

This invention pertains to the asexual reproduction of berry plants, and specifically to the asexual reproduction of a new and distinct variety of strawberry produced by the artificial pollination of the Missionary plant with pollen from the Blakemore strawberry.

The object of the invention is to produce a new variety of strawberry plant which possesses better commercial qualities than varieties now in existence and which is particularly adapted to the soil and climate of the State of Tennessee.

The new variety yields firm fruit of better color and heavier production than the Missionary, which is considered poorly adapted to the soil and climate of the State of Tennessee. It is free from the "yellow leaf" trouble which is so destructive among Blakemore plants and its fruit is of marketable size throughout the picking season.

In the accompanying drawing:

Fig. 1 is a view of a leaf of the plant showing its color and other characteristics;

Fig. 2 is a view of a fruiting stem of the plant showing ripe and green berries and including a view of a blossom showing the blossom characteristics; and Fig. 3 is a longitudinal section of a berry of the new plant showing its internal color and characteristics.

In producing the plant of the present invention, the pollen of the Blakemore strawberry was placed in the blossom of Missionary plants, the pollen-producing parts of the blossoms of the Missionary having first been removed. The pollenated blossoms were then protected so that they could not receive pollen from any other plant, and were allowed to develop into fruit. The seeds from this fruit were then planted and permitted to sprout, and after the plants had grown to sufficient size, they were transplanted and allowed to fruit in the field. At about the time the plants were fruiting in the field each plant and its vegetively developed runner plants were examined for freedom from insects and diseases and for desirable growth habits. The fruit was also tasted and examined for desirable fruit characteristics. The best among a large number of seedlings was then selected and saved and propagated asexually, using runner plants to produce the plant of the present invention. All of the plants which are now growing, including the one from which the accompanying drawing was made, have come from this original seedling.

The new variety differs from its parent varieties in numerous respects. The individual plants are larger than those of Blakemore. Fewer runner plants are developed than in Blakemore. The new variety is not susceptible to the "yellow leaf" trouble which attacks Blakemore. The fruit averages larger in size than the fruit of Blakemore, is less acid, and retains its size throughout the picking season. It is about four days later than Blakemore in season of ripening.

The new variety is less acid than Missionary and the fruit is firmer and of a brighter red color than that of Missionary. The plants grow lower than those of Missionary. The new variety has given good yields under Tennessee conditions unsatisfactory to Missionary. It is particularly adapted to the soil and climate of the State of Tennessee.

One vigorous mother plant of the new variety will produce from a few to more than one hundred runner plants, depending upon soil fertility and growing conditions, and large crops of light red berries will be produced in early season. The foliage of the plant is dense, the leaves are medium in size with thick petioles. Some leaf blight and leaf spot have been noted but the foliage is camparatively healthy.

The berries produced by this plant are medium in size and retain their size throughout the season. They are conic in shape and somewhat necked, smoothly formed, regular and uniform. The surface of the berry is glossy, evenly colored light red and rarely shows green tips. The flesh is very firm, medium juicy, and of a medium red in color, becoming somewhat whitish toward the center. The fruit is sub-acid to tart, good in flavor and firm.

Other characteristics of the new variety are as follows:

Plants: Medium in number. Medium in vigor. Medium height. Very productive. Spring-bearing.

Susceptibility:

*Insects.*—Weevil (sometimes serious).

*Diseases.*—Some blight and leaf spot.

Runners: Medium in thickness. Medium in length. Internodes medium.

Leaves: Medium in size. Medium green. Rugose. Glossy.

Petiole: Thick.

Flowers: Perfect.

*Date of bloom.*—April 13, 1941.

*Length of blooming season.* 33 days.

*Size.*—Diameter 1 inch. Medium.

Picking quality: Very good.

Shipping quality: Very good. Medium in size. Retains size. Uniform fruits. Regular in shape. Conic. Necked.
Apex: Pointed. Rarely green tipped.
Surface color: Light red. Glossy. Attractive. Colors evenly.
Calyx: Medium in size. Raised.
*Color.*—Light green.
*Adherence to fruit.*—Good.
Sepals: Medium in length. Narrow.
Seeds: Medium in number. Sunken.
Petals: Number 5 to 7. Medium in size.
Stamens: Numerous.
Receptacle: Small.
Fruit-stems: Long. Medium in thickness. Erect.
Pedicels: Medium length. Medium thickness.
Fruit:
*Season.*—Early.
Date of ripening: May 7, 1941.
Length of season: All of May.
Flesh: Medium red. Whitish towards center. Medium juicy. Firm. Subacid. Sprightly.
Quality: Good.
Use: Kitchen. Market.
Desirability: Good for shipping.
Remarks: Very firm, uniform, light colored berry that sizes up well and retains its size throughout the season. Medium plant maker, but plants are vigorous.
Classification: Strawberry.

What is claimed is:

A healthy, prolific, fruiting strawberry plant variety substantially as illustrated and described, characterized by subacid, well flavored fruits which are medium red throughout, and by the development of a large number of runner plants.

BROOKS D. DRAIN.